United States Patent [19]
Slocum

[11] Patent Number: 5,304,180
[45] Date of Patent: Apr. 19, 1994

[54] TIBIAL OSTEOTOMY FIXATION PLATE

[76] Inventor: D. Barclay Slocum, 241 Spy Glass Dr., Eugene, Oreg. 97401

[21] Appl. No.: 57,422

[22] Filed: May 4, 1993

Related U.S. Application Data

[63] Continuation of Ser. No. 822,402, Jan. 17, 1992, abandoned.

[51] Int. Cl.$^5$ .............................................. A61B 17/56
[52] U.S. Cl. ......................................... 606/69; 606/71
[58] Field of Search ..................................... 606/69–71, 606/61, 65, 72, 73, 74, 75–77

[56] References Cited

U.S. PATENT DOCUMENTS

| | | | |
|---|---|---|---|
| Re. 28,841 | 6/1976 | Allgower et al. | |
| 3,716,050 | 2/1973 | Johnston | 606/69 |
| 3,824,995 | 7/1974 | Getscher et al. | |
| 4,120,298 | 10/1978 | Fixel | |
| 4,454,876 | 6/1984 | Mears | |
| 4,565,193 | 1/1986 | Streil | 606/69 |
| 4,762,123 | 8/1988 | Slocum | |
| 4,867,144 | 9/1989 | Karas | 606/69 |
| 4,957,497 | 9/1990 | Hoogland | 606/71 |
| 4,959,065 | 9/1990 | Arnett | 606/69 |
| 4,988,350 | 1/1991 | Herzberg | 606/65 |
| 5,002,544 | 3/1991 | Klaue | 606/69 |
| 5,006,120 | 4/1991 | Carter | 606/69 |
| 5,015,248 | 5/1991 | Burstein | 606/69 |
| 5,085,660 | 2/1992 | Lin | 606/69 |
| 5,087,260 | 2/1992 | Fixel | 606/69 |

FOREIGN PATENT DOCUMENTS

| | | | |
|---|---|---|---|
| 0207884 | 1/1987 | European Pat. Off. | 606/69 |
| 2806414 | 6/1981 | Fed. Rep. of Germany | |
| 2472373 | 7/1981 | France | 606/69 |
| 2556583 | 6/1985 | France | 606/69 |
| 2606268 | 5/1988 | France | 606/65 |

Primary Examiner—Michael A. Brown
Attorney, Agent, or Firm—Kolisch Hartwell Dickinson McCormack & Heuser

[57] ABSTRACT

An elongate tibial plateau-leveling osteotomy fixation plate is disclosed. The plate generally conforms in three dimensions to the proximal tibial segment and metaphysis that are separated and rotated for such fixation. The plate has formed therein six holes, three in a proximal triangular expanse overlying the metaphysis and three in a distal elongate expanse overlying the proximal tibia, with the cylindrical osteotomy lying between these sets of holes. Two of the holes in the triangular expanse are elongate, with their long axes intersecting at the center of the curvilinear osteotomy. The two elongate holes include in their circular ends oppositely 45° beveled features that allow the plate, when secured by fasteners or screws in all six holes, compressibly or distractably to urge the proximal tibia and the metaphysis together or apart along a radius of the osteotomy that generally bisects the arc of the curvilinear cut, or neutrally to fix them in a position of neither compression nor distraction. All six holes include in their remaining regions arcuately curved "countersink" beveled features that conform with the curved head of the screws with which the plate is fixed to the osteotomy site. The compressive/distractive forces incident to securing one or more screws through the elongate hole(s) into the metaphysis cooperate with the forces incident to securing one or more screws through the round hole(s) into the proximal tibia, thereby better to fix the plate against inadvertent movement relative to either section.

16 Claims, 2 Drawing Sheets

TIBIAL OSTEOTOMY FIXATION PLATE

This is a continuation of application Ser. No. 07/822,402 filed Jan. 17, 1992, now abandoned.

BACKGROUND AND SUMMARY OF THE INVENTION

The invention relates generally to fixation of cut and rotated bone portions following a proximal, tibial osteotomy. More particularly, the invention concerns a fixation plate and fasteners for use in fixing the proximal tibial and metaphyseal tibial portions as a final step in performing a tibial plateau-leveling curvilinear-cut and rotate osteotomy.

A proximal tibial osteotomy for leveling a canine's tibial plateau involves producing in the proximal tibia a curvilinear through cut that separates the metaphysis from the proximal tibia, rotating the metaphysis relative to the proximal tibia a predetermined amount that effectively levels the tibial plateau and fixing the metaphysis relative to the proximal tibia by suitable means. Such an osteotomy is described in detail in my U.S. Pat. No. 4,677,973 entitled "Proximal, Tibial Osteotomy for Leveling A Tibial Plateau", which issued Jul. 7, 1987, the disclosure of which is incorporated herein by this reference. While the osteotomy method disclosed therein is effective in leveling the tibial plateau, fixation as by pinning and/or wiring is not always as effective as desired in the short and long-term fixation of the cut and separated, and relatively rotated, tibial portions. Less secure fixation can result in retarded osteosynthesis and, ultimately, failure of the proximal tibia and/or the femoro-tibial joint.

Accordingly, it is a principal object of the present invention to provide a fixation plate and fasteners for use in fixing the relatively rotated bone segments that result from a tibial plateau-leveling osteotomy.

Another object is to provide such a plate that accommodates a wide range of choice in compressively, distractively or neutrally impacting the bone segments in their fixation relative to one another.

Yet another object is to provide such a plate the formed screw holes of which maximally conform along at least one axis, to fasteners used in securing the plate to the osteotomy site.

Another important object of the invention is to provide such a plate that generally conforms in three dimensions to the proximal tibia for which it is particularly suited.

Still another object is to provide such a plate with a plural screw hole configuration that, with fasteners properly inserted therethrough into the bone segments, provides for better securement of the plate to the proximal tibial site due to cooperation among certain of the hole/fastener pairs.

It is also an object of the invention to provide such a fixation plate and fastener set that easily and cost-effectively are manufactured.

In brief summary of the invention, an elongate tibial plateau-leveling osteotomy fixation plate is provided that in cross-sectional view along its long axis is curved to conform along its extent with the differently cross-sectionally curved proximal tibial segment and metaphysis. The plate is shaped and dimensioned in its generally sagittal planar extents to conform in part with the elongate proximal tibia, with a generally triangular, cranially extending expanse at its proximal end. The plate preferably has formed therein six holes, three triangularly arrayed in the triangular proximal expanse overlying the metaphysis and three linearly arrayed in the elongate distal expanse overlying the proximal tibia (with the preferably cylindrical osteotomy cut, separated, relatively rotated and conformingly mating surfaces extending between these sets of holes).

Preferably two of the holes in the triangular expanse are elongate, with their long axes intersecting at the center of the curvilinear osteotomy. The two elongate holes include in their circular ends oppositely 45° beveled features that allow the plate, when secured by screws in all six holes, compressibly or distractably to urge the proximal tibia and the metaphysis together or apart along a radius of the osteotomy that generally bisects the arc of the curvilinear cut, or neutrally to fix them in a position of neither compression nor distraction. All six holes include in their remaining regions arcuately curved "countersink" beveled features that conform precisely with the curved head of the screws with which the plate is fixed to the osteotomy site. The compressive/distractive forces incident to securing one or more screws through the elongate hole(s) into the metaphysis cooperate with the forces incident to securing one or more screws through the round hole(s) into the proximal tibia, thereby better to fix the plate against inadvertent movement relative to either section.

These and other objects and advantages of the invention will be more clearly understood from a consideration of the accompanying drawings and the following description of the preferred embodiment.

BRIEF DESCRIPTION OF THE DRAWINGS

In the interest of clarity, it will be appreciated that the preferred embodiment of the invention is illustrated and described consistently, with respect to orientation, relative to its use in performing a tibial plateau-leveling osteotomy. Thus, the orientation of the plate illustrated in FIGS. 1 through 6 is described using anatomical terminology, as though the plate were positioned in the proximal tibial region on the medial side a patient's left leg and viewed from a vantage point located medially therefrom.

DETAILED DESCRIPTION OF THE PREFERRED EMBODIMENT

Figure 1:
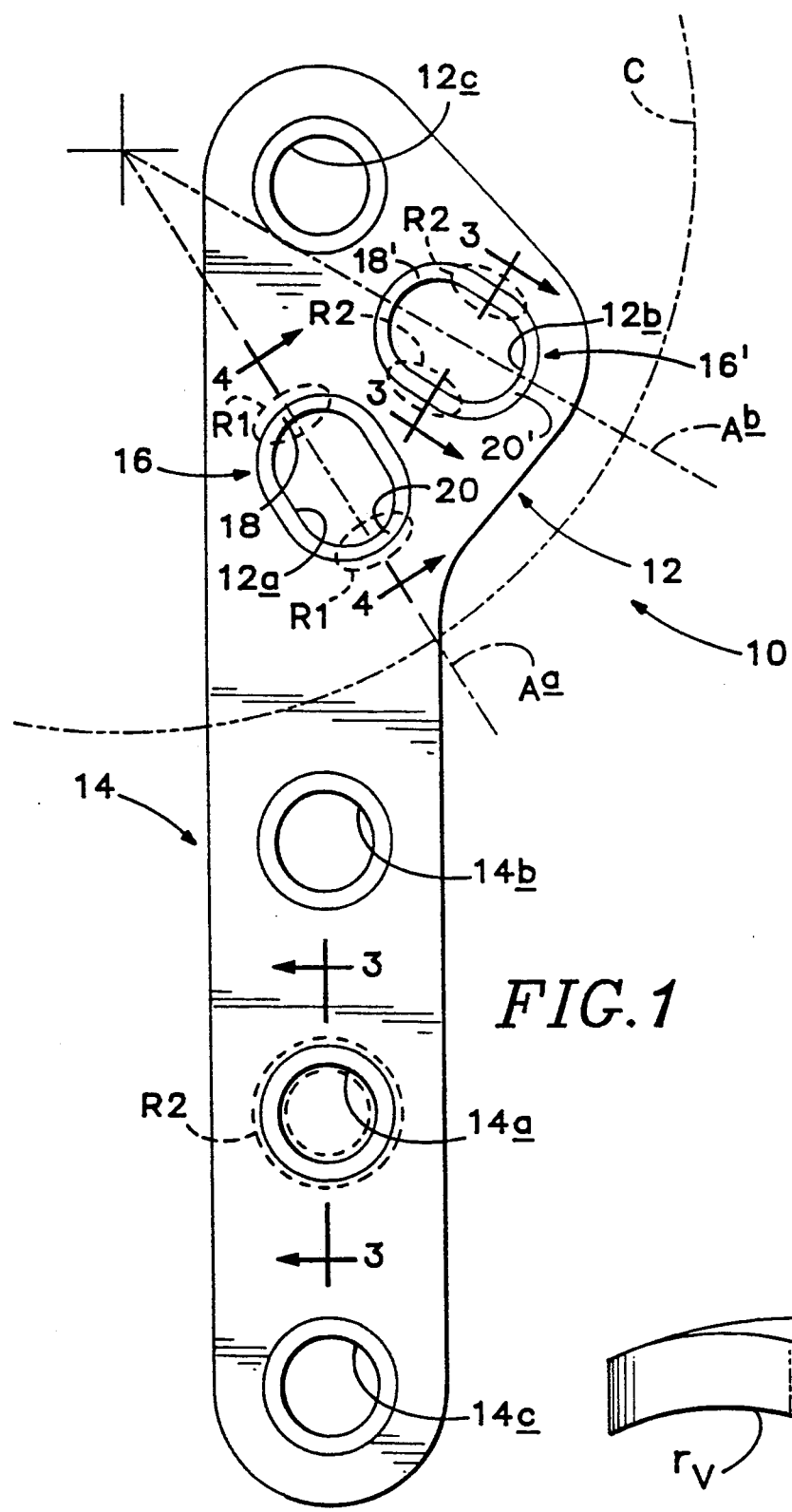
FIG. 1 is a medial view of a left osteotomy fixation plate made in accordance with the preferred embodiment.
Figure 2:
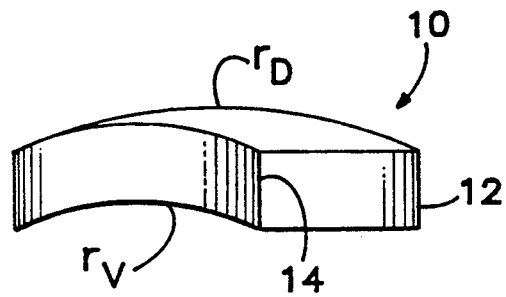
FIG. 2 is a ventral view of the fixation plate corresponding with FIG. 1.

FIGS. 1 and 2 represent medial (front elevational) and ventral (end) views, respectively, of the invented fixation structure, or plate, made in accordance with its preferred embodiment and indicated at 10. It will be understood that fixation structure 10 is useable, in the field of proximal tibial osteotomy apparatus, with fastener elements, e.g. screws not shown in FIGS. 1 and 2 but shown in FIGS. 3 through 5, in fixing two preferably circularly curvilinearly cut, separated and rotated proximal tibial segments. Structure or plate 10 may be seen to comprise first subframe means, or a first generally planar expanse configured for overlying one such tibial segment, 12. Structure or plate 10 may be seen also to comprise second subframe means, or a second generally planar expanse, 14 configured for overlying the other such tibial segment, the second subframe means or expanse 14 being rigidly joined to and operable as a unit with first subframe means or expanse 12 in substantially coplanar relation therewith.

First subframe means or expanse 12 includes at least a first elongate hole, or drive aperture, 12a the long axis of which is oriented substantially to intersect the center (+) of such circularly curvilinear cut C indicated in FIG. 1 by a dash-dot-dot line. Preferably, expanse 12 also has formed therein a second elongate hole, or drive aperture, 12b the long axis of which is oriented substantially to intersect the long axis of first elongate hole, or drive aperture, 12a substantially at the center (+) of curvilinear cut C.

Each of elongate holes, or drive apertures, 12a, 12b may be seen to define what will be referred to herein as a cut-radial drive axis such a first cut-radial drive axis Aa associated with drive aperture 12a and may be thought of as having what will be referred to herein as differentiated-direction, selectable drive-interaction means 16. Drive-interaction means 16 within a first region R1 around elongate hole 12a preferably includes compression-effecting means, or a preferably approximately 45° inclined chamfer, 18 for urging such one tibial segment toward another tibial segment generally along first cut-radial drive axis Aa, or long axis of hole 12a, during securement of fixation structure or plate 10 to the segments.

Figure 4:
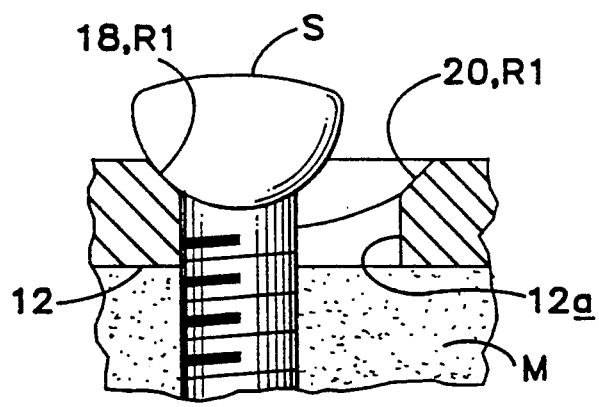
FIG. 4 is a cross-sectional view of the plate taken generally along either of the lines 4—4 of FIG. 1 showing such slotted hole in side view.

Brief reference to FIG. 4 best illustrates this compression effect whereby it may be seen that as a screw S is secured in a tibial segment such as metaphysis M, a working lower surface, or underside, of the head of screw S impacts upon chamfer 18 and effectively urges expanse 12 and metaphysis M in opposite directions, i.e. the tendency is for expanse 12 to move to the left in FIG. 4 and for metaphysis M to move to the right therein. It will be appreciated that, were screw S to be placed near the opposite end of elongate hole 12a, the drive interaction would be characterized as producing a distraction effect in which as screw S were driven into metaphysis M, an underside of the head of screw S would impact upon preferably equally and oppositely, and most preferably 45°, inclined chamfer 20 and effectively would urge expanse 12 and metaphysis M in reverse opposite directions, i.e. the tendency would be for expanse 12 to move to the right in FIG. 4 and for metaphysis M to move to the left therein. Thus, a region such as chamfer 20 around first elongate hole 12a includes what will be described herein as distraction-effecting means for urging one tibial segment such as metaphysis M away from another tibial segment such as proximal tibia T generally along long axis Aa of hole 12a during securement of fixation structure or plate 10 to the segments, as will be seen by reference to FIG. 5.

It will be appreciated that, were screw S placed halfway between the opposite ends of elongate hole 12a, or approximately in its center, there would be no effective compression and no effective distraction. Thus, drive-interaction means 16 is characterized as being differentiated-directional and selectable: depending on the location of the fastener element, e.g. screw S, within drive aperture 12a. drive-interaction means 16 selectively urges (urges or not) and if so then independently urges (one or the other but not both of) compression and distraction of the cut, separated and relatively rotated tibial segments along cut-radial drive axis Aa.

Figure 3:
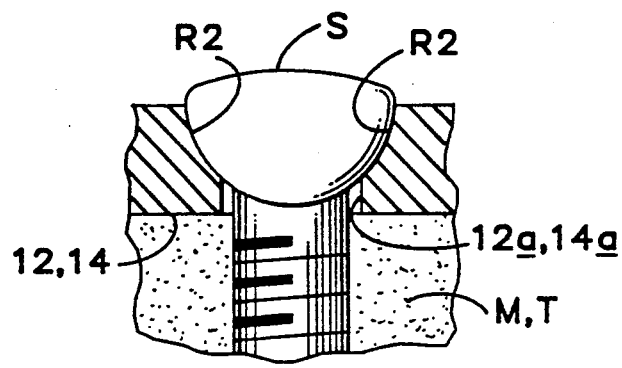
FIG. 3 is a cross-sectional view of the plate taken generally along either of the lines 3—3 of FIG. 1 showing one of the slotted holes in end view and showing one of the round holes in side view.

Referring still to FIGS. 1 and 2, second subframe means, or expanse, 14 includes at least a first anchor aperture, or round hole, 14a dimensioned to receive a screw such as screw S therethrough, as may be seen by brief reference to FIG. 3. Preferably, a wall region R2 of round hole 14a is formed conformingly to engage a underside head region of screw S around its substantial periphery. In accordance with the preferred embodiment of the invention, first subframe means, or expanse, 12 has formed therein a second round hole 12c dimensioned to receive a screw such as screw S therethrough. Preferably identical to first round hole 14a formed in expanse 14, second round hole 12c formed in plate 10 has a wall region R2 (shown but not designated in FIG. 1) that is formed conformingly to engage an underside head region of screw S around its substantial periphery.

Also in accordance with the preferred embodiment of the invention, fixation structure or plate 10 comprises at least a third and most preferably a third and a fourth anchor aperture, or round hole, 14b, 14c, which are identical with first and second round holes 14a, 12c. Preferably, third and fourth round holes 14b, 14c are approximately equally spaced on either side of round hole 14a such that the three round holes formed in second expanse 14 are regularly spaced or arranged in a row extending along the substantial extent of expanse 14, as best shown in FIG. 1. This arrangement of plural round holes in expanse 14 enables fixation structure or plate 10 securely to be anchored to the cut, separated and relatively rotated proximal tibia, as will be seen by reference to FIG. 5.

Referring still to FIG. 1, it is reiterated that second drive aperture, or elongate hole, 12b formed in first subframe means, or expanse, 12 preferably includes differentiated-direction, selectable drive-interaction means 16', which is identically structured to but differently oriented from drive interaction means 16 associated with first elongate hole 12a. From FIG. 1 it may be seen that elongate hole 12b by its orientation in first expanse 12 defines a second cut-radial drive axis Ab that is oriented at an angle relative to drive axis Aa. Importantly, first and second drive axes Aa, Ag extend radially relative to the center (+) of circular cut C at which they intersect. The beneficial result is that they intersect cut C perpendicular to tangents defined thereby. As will be seen by reference to FIG. 5, when fixation structure or plate 10 is anchored to two cut, separated and relatively rotated tibial segments, the selected compressional or distractional urging of the two segments occurs along different radial axes both of which are normal to the circularly curvilinear cut surface.

Figure 5:
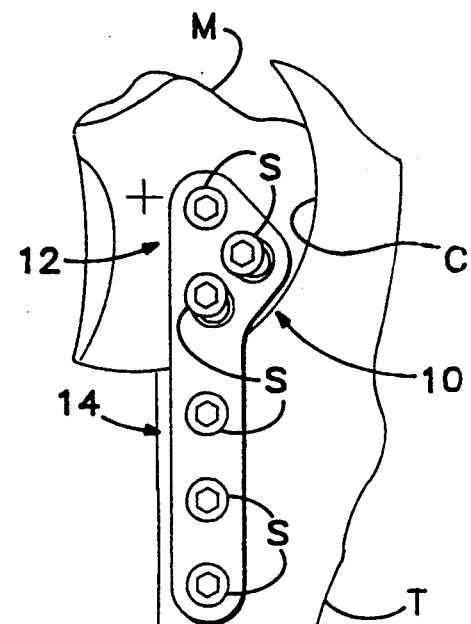
FIG. 5 is a medial view showing fragmentarily a canine's proximal tibial region with the fixation plate anchoring the curvilinearly cut and rotated tibial and metaphysis portions.

As may be surmised, drive-interaction means 16' includes a region such as a chamfer 18' around second elongate hole 12b that includes compression-effecting means for urging one tibial segment such as metaphysis M toward the other tibial segment such as proximal tibia T generally along second drive axis, or the long axis of second elongate hole 12b, Ab during securement of fixation structure or plate 10 to the segments, as will be seen by reference to FIG. 5. Complementarily, and to opposite effect, drive-interaction means 16' includes a region such as a chamfer 20' around second elongate hole 12b that includes distraction-effecting means for urging metaphysis M away from proximal tibia T generally along long axis Ab of second elongate hole 12b during securement of fixation structure or plate 10 to the segments, as will be seen.

Referring now to FIG. 5, a first of two cut, separated and relatively rotated tibial sections such as metaphysis M includes a convex curvilinear cut C that may be seen to define a central cylindrical axis (+), and a second of the two tibial sections such as proximal tibia T may be seen to include a conforming concave curvilinear cut C produced, for example, by an oscillating cylindrical saw blade. In accordance with the practice of the proximal tibial osteotomy, cut and separated metaphysis M has been rotated through an angle that effectively and beneficially levels the tibial plateau in accordance with the teachings of my U.S. Pat. No. 4,677,973.

Briefly summarizing the above description, first expanse 12 configured for overlying metaphysis M includes plural holes 12a, 12b, 12c formed therein for receiving fixation screws S and second expanse 14 configured for overlying proximal tibia T includes plural holes 14a, 14b, 14c formed therein also for receiving fixation screws S. At least one of the holes, and preferably two, is elongate and has a long axis that intersects the cylindrical axis (+) when fixation plate 10 is secured as shown in FIG. 5 to the tibial sections in the described overlying regions thereto. Those of skill in the arts will appreciate that, by the provision in one or more elongate holes formed preferably in metaphysis overlying expanse 12 of selectively operable compression-effecting means such as chamfer 18 and distraction-effecting means such as chamfer 20, the tibial sections can be urged relative to one another substantially along the long axis of the elongate hole, e.g. axis Aa, during securement of the fixation plate to the tibial sections.

Chamfers, or beveled regions, 18, 20 may be seen by reference to FIGS. 4 and 5 to provide for the generally equal and opposite urging of such tibial sections, depending upon the selective placement of a fixation screw such as screw S adjacent one or the other of the beveled regions. FIG. 5 illustrates a placement of screws S adjacent bevels 18, 18' of elongate holes 12a, 12b, such that, with expanse 14 securely anchored to proximal tibia T, tightening of those screws within holes 12a, 12b effectively urges metaphysis M simultaneously along axes Aa, Ab into compressive engagement with proximal tibia T at two distinct arcuate locations along circularly curvilinear cut C. Such compression has been found advantageously to securely anchor the tibial sections in the desired angular configuration, and to promote osteosynthesis and healing.

Referring now collectively to FIGS. 2 and 5, it will be understood that expanse 4 defines a ventral region of fixation plate 10 that, in ventral view (i.e. a view generally axially along tibia T toward the femur (not shown)) is slightly curved in an arc of radius $r_v$, whereas expanse 12 defines a dorsal region of plate 10 that in ventral view is also slightly curved, but in an arc of different, preferably larger radius $r_D$. The curvature of the dorsal and ventral regions is perhaps best shown in FIG. 2 such that the respective regions effectively curve transversely around the long axes of proximal tibia T and metaphysis M. The dorsal region defined by expanse 12 may be seen to be generally triangular shaped, while the ventral region defined by expanse 14 is seen to be generally linearly longitudinally shaped. Thus, fixation structure or plate 10 is formed preferably substantially to conform in three dimensions to the to-be-fixed proximal tibial and metaphysis sections.

Such three dimensional conformation also has been found advantageously to provide for the secure anchoring of plate 10 to the osteotomy site and to promote osteosynthesis. Moreover, within the generally triangular shaped dorsal region defined by expanse 12, elongate hole pair 12a, 12b and round hole 12c formed therein are triangularly arrayed in the dorsal region of expanse 12 in substantial congruity with the triangular shape thereof. Such arrangement is believed optimally to distribute the substantial load that is borne by fixation structure or plate 10 over the tibial sections impacted thereby.

FIG. 3 perhaps best illustrates the fact that all holes, whether round or elongate, formed in fixation structure or plate 10 are dimensioned and beveled to receive therein fixation screws S in countersunk relationship to the holes. Notably, round holes 12c, 14a, 14b, 14c are beveled in such manner as to conform to the underside, mating surface of fixation screw S everywhere, while elongate holes 12a, 12b are beveled, or provided with bevels inclined, differentially between the long axis of the hole and an axis transverse thereto. As a result, when a screw S is tightened against either end of an elongate hole such as hole 12a, compression or distraction along axis Aa is effected, while unyielding securement is effected by the countersunk relationship between screw S and regions R2 along an axis transverse to axis Aa. This is why FIG. 3 is illustrated as being descriptive not only of round hole 14a but also of elongate hole 12b in a view taken along axis Ab.

Those of skill in the arts will appreciate that the advantage of forming beveled regions R2 to conform precisely with the underside of the head of screws S is that, once they are tightened, screws S must be backed out in order to unfasten fixation structure or plate 10 and the joined tibial sections. The precise machining of beveled regions R1, R2 is accomplished, for example, by precisely controlling the path of a ball mill during the manufacture of plate 10.

In use, fixation plate 10 is secured to the cut, separated and relatively rotated tibial segments M, T preferably as briefly follows, with respect to the compression-effecting arrangement shown in FIG. 5. First, screws S are secured in holes 14b, 14c, 14a, preferably but not necessarily in that order. Next, screws S are secured in holes 12b and 12a. This securing step usually is performed in the listed order because usually it is found that the larger gap between segments M, T resulting from a less than perfect cut is closer to hole 12b than it is to hole 12a. The effect of securing screw S in hole 12b first is that metaphysis M is urged (to the right in FIG. 5) into proper compression fit with proximal tibia T as against any undesirable gap. It has been found that compression along an axis generally transverse to the tibia's long axis is both more important and more difficult to achieve than is compression along the axis. Thus, it is believed that securement of hole 12b generally should be performed prior to that of hole 12a. Finally, screw S is secured in hole 12c to set or secure the positions of screws S relative to elongate holes 12a, 12b in plate 10, thereby to maintain the compression effected thereby during healing of the osteotomy site. It will be appreciated that securement to effect distraction in accordance with the invention, or to effect neither compression nor distraction, may be accomplished similarly, although the order in which securement is accomplished may vary.

Accordingly, while a preferred embodiment of the invention has been described herein, it is appreciated that modifications are possible that are within the scope of the invention.

It is claimed and desired to secure by letters patent:

1. A fixation structure for fixing two segments of a whole wherein the segments are produced by a curvilinear cut, the structure comprising:

first subframe means including plural elongate drive apertures defining angle-differentiated cut-radial drive axes oriented generally normal to such curvilinear cut at different locations therealong, each of said apertures having differentiated-direction, selectable drive-interaction means; and second subframe means joined to and operable as a unit with said first subframe means including an anchor aperture;

each of said drive-interaction means of said structure including a fastener element received within and through each of said aperture and anchored to one of such segments, and being operable, depending on the location of such element within said drive aperture, selectively and independently to urge compression and distraction of such segments along said corresponding axis.

2. A fixation plate for use in fixing two circularly curvilinearly cut, separated and rotated proximal tibial segments comprising:

a first generally planar expanse configured for overlying one such tibial segment, said expanse including a first elongate hole the long axis of which is oriented substantially to intersect the center of such circularly curvilinear cut, and a second generally planar expanse rigidly joined with said first expanse in substantially coplanar relation therewith, said second expanse defining a long axis of the fixation plate and being configured for overlying the other such tibial segment, said second expanse including a first round hole dimensioned to receive a screw therethrough, a wall region of said first hole being formed conformingly to engage a lower head region of such screw around the substantial periphery thereof, a region around said first elongate hole including compression-effecting means for urging such one tibial segment toward another tibial segment generally along the long axis of said first elongate hole during securement of the plate to the segments, with the long axis of said first elongate hole extending at an acute angle relative to the long axis of the fixation plate.

3. The plate of claim 2 further comprising a second round hole formed in said first expanse dimensioned to receive a screw therethrough, with a wall region of said second hole being formed conformingly to engage a lower head region of such screw around the substantial periphery thereof.

4. The plate of claim 2 further comprising a second elongate hole formed in said first expanse the long axis of which is oriented substantially to intersect the long axis of said first elongate hole substantially at the center of such circularly curvilinear cut.

5. The plate of claim 4 wherein a region around said second elongate hole includes compression-effecting means for urging such one tibial segment toward such other tibial segment generally along the long axis of said second elongate hole during securement of the plate to the segments.

6. The plate of claim 2 wherein a region around said first elongate hole further includes distraction-effecting means for urging such one tibial segment away from another tibial segment generally along the long axis of said first elongate hole during securement of the plate to the segments.

7. The plate of claim 6 further comprising a second elongate hole formed in said first expanse the long axis of which is oriented substantially to intersect the long axis of said first elongate hole substantially at the center of such circularly curvilinear cut, wherein a region around said second elongate hole includes distraction-effecting means for urging such one tibial segment away from such other tibial segment generally along the long axis of said second elongate hole during securement of the plate to the segments.

8. In the field of proximal tibial osteotomy apparatus used to orient two cut, separated and relatively rotated tibial sections, wherein a first section includes a convex curvilinear cut that defines a central cylindrical axis and wherein a second section includes a conforming concave curvilinear cut, a fixation plate comprising:

a first expanse configured for overlying such first tibial section, said first expanse including plural holes formed therein for receiving fixation screws;

a second elongate expanse rigidly joined with said first expanse, said second expanse being configured for overlying a long axis of such second tibial section, said second expanse including plural holes formed therein for receiving fixation screws;

at least one of said holes in said first expanse being elongate, said elongate hole having a long axis that extends transversely to said long axis of said second elongate expanse and intersects such cylindrical axis when said plate is secured to the sections in said overlying relations to such tibial sections, wherein a region around said elongate hole includes selectively operable compression-effecting means and distraction-effecting means for urging such tibial sections relative to one another substantially along the long axis of said elongate hole during securement of the plate to such tibial sections.

9. The plate of claim 8 wherein said selectively operable compression-effecting and distraction-effecting means includes beveled regions formed in the ends of said elongate hole, said beveled regions providing for the generally equal and opposite urging of such tibial sections depending upon the selective placement of such fixation screw adjacent one of said beveled regions.

10. A fixation plate for use in fixing curvilinear cut, separated and rotated proximal tibial and metaphysis sections, with the cut being cylindrical and defining a central elongate axis of the cylinder, the plate comprising:

a generally planar expanse having an elongate ventral region for overlying such proximal tibial section and a dorsal region for overlying such to-be-fixed metaphysis section, said expanse having formed in said ventral region plural round holes each dimensioned and beveled to receive countersunk therein a fixation screw;

said expanse having formed in said dorsal region a round hole dimensioned and beveled to receive countersunk therein a fixation screw, said expanse having further formed in said dorsal region an elongate hole having a long axis dimensioned and provided with a first pair of beveled regions along an axis transverse to a long axis thereof to receive countersunk therein a fixation screw, said elongate hole being dimensioned and provided with a second pair of beveled regions along said long axis inclined differentially from the inclination of said first pair of beveled regions to accommodate the selective placement of such fixation screw along said long axis, said second pair of beveled regions selectively providing, when confronted by a working lower surface of the head of such fixation screw, for the substantially equal and opposite urging of said plate relative to such to-be-fixed metaphysis section during securement of said plate to such sections.

11. The plate of claim 10, wherein said dorsal region of said expanse is generally triangularly shaped, wherein said ventral region of said expanse is generally linearly longitudinally shaped and wherein said dorsal and said ventral regions of said expanse are slightly curved, in arcs having different radii, around the long axes of such proximal tibial section and such metaphysis, thereby substantially to conform said plate in three dimensions to the to-be-fixed proximal tibial and metaphysis sections.

12. The plate of claim 11, wherein said dorsal region of said expanse has formed therein a pair of said elongate holes, wherein said elongate holes and said round hole formed in said dorsal region are triangularly arrayed in said dorsal region of said expanse and wherein said elongate holes are oriented such that their long axes intersect one another substantially at such central axis of the cylinder.

13. A fixation plate for fixing two curvilinearly cut and separated bone segments, the plate comprising:
a first expanse having formed therein plural elongate holes for receiving fastener elements therethrough into a first bone segment, at least two of said elongate holes defining axes normal to the curvilinear cut at arcuately spaced points therealong;
a second expanse rigidly joined to and operable as a unit with said first expanse, said second expanse including an anchor hole for receiving a fastener element therethrough into a second bone segment;
said two elongate holes each having a beveled region on an end thereof away from the cut made to interact with a corresponding fastener element such that tightening of the latter against such first beveled region urges the firs bone segment toward the second bone segment to produce cut-normal compression in spaced regions thereof corresponding to such arcuately spaced points along the curvilinear cut separating the bone segments.

14. The plate of claim 13 with said two elongate hole each further having a second beveled region on an end thereof toward the cut made to interact with such corresponding fastener element such that tightening of the latter against said second beveled region urges the first bone segment away from the second bone segment to product cut-normal distraction in spaced regions thereof corresponding to such arcuately spaced points along such curvilinear cut.

15. A fixation plate for use in fixing curvilinear cut, separated and rotated proximal tibial and metaphysis section, with the cut being cylindrical and defining a central elongate axis of the cylinder, the plate comprising:
a generally planar expanse having an elongate ventral region for overlying such proximal tibial section and a dorsal region for overlying such to-be-fixed metaphysis section,
said expanse having formed in said ventral region plural holes each dimensioned and beveled to receive counter sunk therein a fixation screw;
said expanse having formed in said dorsal region a drive aperture dimensioned and provided with a first pair of beveled regions to receive counter sunk therein a fixation screw, and said drive aperture being further dimensioned and provided with a second pair of beveled regions inclined differentially from the inclination of said first pair of beveled regions to accommodate the selective placement of such fixation screw, said second pair of beveled regions selectively providing, when confronted by a working lower surface of the head of such fixation screw, for the urging of said plate, substantially equally and oppositely relative to such to-be-fixed metaphysis section, during securement of said plate to such sections.

16. The plate of claim 15, wherein said dorsal region of said expanse is generally triangularly shaped, wherein said ventral region of said expanse is generally linearly longitudinally shaped and wherein said dorsal and said ventral regions of said expanse are slightly curved around the long axes of such proximal tibial section and such metaphysis, thereby substantially to conform said plate in three dimensions to the to-be-fixed proximal tibial and metaphysis sections.

* * * * *